US007378570B1

(12) United States Patent
Lambeth et al.

(10) Patent No.: US 7,378,570 B1
(45) Date of Patent: May 27, 2008

(54) POLLEN POLYMIX PLANT BREEDING METHOD UTILIZING MOLECULAR PEDIGREE ANALYSIS

(75) Inventors: Clements C. Lambeth, Hot Springs, AR (US); Nicholas C. Wheeler, Centralia, WA (US)

(73) Assignee: Weyerhaeuser Co., Federal Way, WA (US)

( * ) Notice: Subject to any disclaimer, the term of this patent is extended or adjusted under 35 U.S.C. 154(b) by 82 days.

(21) Appl. No.: 09/618,307

(22) Filed: Jul. 18, 2000

(51) Int. Cl.
*A01H 1/02* (2006.01)
*A01H 1/04* (2006.01)
*C12N 15/10* (2006.01)

(52) U.S. Cl. ............... 800/267; 800/265; 800/271; 800/319

(58) Field of Classification Search .............. 800/260, 800/266, 267, 271, 319, 315, 323, 316
See application file for complete search history.

(56) References Cited

U.S. PATENT DOCUMENTS 5,981,832 A    11/1999    Johnson

FOREIGN PATENT DOCUMENTS

EP    0483514 A1    9/1991

OTHER PUBLICATIONS

Straws et al. Can. J. For. Res. 22:1050-1061, 1992.*
Rogers et al. Heredity 67(3):373-379, 1991.*
Moran et al. Silvae Genetica 34(4-5):117-121, 1985.*
Wiselogel et al. Silvae Genetica 37(5-6):184-187, 1988.*
Stoehr et al. Can. J. For. Res. 28(3):418-426, 1998.*
El-Kassaby et al. Theor. Appl. Genet. 83(6-7):752-758, 1992.*
Lambeth et al. Theor. Appl. Genet. 103:930-943 (2001).*
Grattapaglia et al. Theoretical and Applied Genetics 109: 192-199 (2004).*
de Castro et al. Poster: SSR analysis of pollen parent fitness in polymix crosses of *Eucalyptus grandis* and *E. urophylla* (2004).*
Purvis et al. Research Report: Report on an Evaluation of Alternative Pine Breeding Strategies (Jan. 2002).*
Wheeler et al. Tree Genetics & Genomes 2: 53-60 (2006).*
Shelbourne, C.J.A. Forest Research Institute: New Zealand Forest Service Technical Paper 55: 1-43 (1969).*
Burdon et al. pp. 75-85 In: Forest Genetics and Tree Breeding in the Age of Genomics: 2004 IUFRO Forest Genetics Meeting Proceedings, Bailian et al, eds. , IUFRO Joint Conference: Charleston NC (2004).*
Burdon et al. N.Z. Journal of Forestry Science 1(2): 174-193 (1971).*
McKeand et al. pp. 234-240 In: IUFRO Conference: Breeding Tropical Trees, CAMCORE: Cartagena, Columbia (Oct. 1992).*
Burdon et al. Canadian Journal of Forestry Research 20: 1664-1671 (1990).*
Kumar, S. Email correspondence of Jul. 20, 2006.*
Burdon and van Buijtenen, *Can. J. For. Res.* 20:1664-1671 (1990).

White, In: *Proc QFRI-IUFRO Conf, Tree Improvement for Sustainable Tropical Forestry*, Caloundra, Australia, pp. 110-117 (1996).
Cotterill, *Silv. Genet.* 35(5-6):212-223 (1986).
Burden and Shelbourne, *NZ J. For. Sci.*, 1(2):174-193 (1971).
Kerr, *Theor. Appl. Genet.* 96:484-493 (1998).
Shelbourne, Tech. Pap No. 55, New Zealand Forest Service, 44 pp. (1969).
Bridgwater, In: Fins et al. (eds.). *Handbook of Qualitative Forest Genetics*, Kluwer Academic Pub., Dordrect, The Netherlands. pp. 69-95 (1992).
Huber et al., *For. Sci.* 38(4):757-776 (1992).
Janssens, *Silv. Gen.* 29(3-4):138-140 (1980).
Lowe and van Buijtenen, In: *Proc. IUFRO Conf on Breeding and Testing Theory, Progeny Testing and Seed Orchards*, Williamsburg, Virginia, pp. 98-106 (1986).
McKeand and Bridgwater, In: *Proc. IUFRO Resolving Tropical Forest Resource Concerns Through Tree Improvement, Gene Conservation, and Domestication of New Species*, Cali, Colombia, pp. 234-240 (1992).
White et al., *Silv. Genet.*, 42:359-371 (1993).
Isagi et al., *Heredity*, 84:143-151 (2000).
Nakamura and Wheeler, *Evolution*, 46(3):846-851 (1992).
Wheeler and Jech, *New Forests*, 6:311-328 (1992).
Advances in Pollen Management, U.S.D.A. Forest Service Agriculture Handbook, No. 698:55-63 (1993).
Groover et al., *Genetics* 138:1293-1300 (1994).
O'Malley and McKeand, *For. Gen* 1:207-218 (1994).
O'Malley et al., In: Genomes of Plants and Animals: $21^{st}$ Stadler Genetics Symposium, Gustafson and Flavell (eds.). Plenum Press, New York (1996), pp. 87-102.
Staub et al. *HortScience* 31(5):729-740 (1996).
Cervera et al., *Plant Growth Regulation*, 20:47-52 (1996).

(Continued)

*Primary Examiner*—David T Fox
(74) *Attorney, Agent, or Firm*—Christensen O'Connor Johnson Kindness

(57) ABSTRACT

The present invention is directed to a plant breeding and testing method that utilizes a pollen mixture derived from many male parents in conjunction with field trials and molecular pedigree analysis to evaluate breeding values and make progeny selections for the next generation of breeding. More specifically the plant breeding method involves mixing pollen obtained from a breeding group composed of a plurality of parental plants to obtain a pollen polymix. The polymix is used to pollinate female reproductive structures from parental plants in the breeding group to obtain a plurality of progeny seed lots. Each progeny seed lot has seeds obtained from a different cross between the pollen polymix and a different parental plant. Resultant progeny plants from each seed lot are evaluated using objective criteria to obtain a phenotype score. The pedigree of at least some of the progeny plants, usually those with a desirable phenotype score, is determined using molecular parental analysis. Lastly, the pedigree and phenotype score are used to identify elite plants for use in a next generation of plant breeding.

13 Claims, No Drawings

OTHER PUBLICATIONS

Dinus and Tuskan, In: *Micropropagation, genetic engineering and molecular biology of Populus*, Ed., Klopfenstein et al. USDA Forest Service Gen. Tech. Rep. RM-GTR-297, p. 220-235 (1997).

Stoehr et al., *Can. J. For. Res.*, 28:187-195 (1998).

Ziegenhagen et al., *Can. J. For. Res.* 28:317-321 (1998).

Smouse and Meagher, *Genetics*, 136:313-332 (1994).

Marshall et al., Mol. Ecol. 7:639-655 (1998).

Goodnight and Queller, *Mol. Ecol.*, 8:1231-1234 (1999).

Double et al., *Mol. Ecol.* 6:115-1166 (1997).

Grob, J.A., et al., "Dimensional Model of Zygotic Douglas-Fir Embryo Development," *Int. J. Plant Sci.* 160(4):653-662, 1999.

Timmis, R., "Bioprocessing for Tree Production in the Forest Industry: Conifer Somatic Embryogenesis," *Biotechnology Progress* 14(1):156-166, Feb. 1998.

"Pine Mapping Projects—North America," *National Agricultural Library, U.S. Department of Agriculture*, Mar. 1995, <http://www.nal.usda.gov/pgdic/Map_proj/pine.html> [retrieved Apr. 25, 2002].

Burdon, R.D., and C.J.A., Shelbourne, "Breeding Populations for Recurrent Selection: Conflicts and Possible Solutions," *N.Z. Jl. For. Sci.* 1(2):174-193, Jun. 16, 1971.

Chen, D.M., and L.F. De Filippis, "Application of Genomic DNA and RAPD-PCR in Genetic Analysis and Fingerprinting of Various Species of Woody Trees," *Australian Forestry* 59(1):46-55, Feb. 20, 1996.

Dale, G., and B. Teasdale, "Strategies for Efficient Application of Market-Assisted Breeding in Tree Improvement," *Proceedings of IUFRO '97 Genetics of Radiata Pine*, Rotorua, New Zealand, Dec. 1-4, 1997, FRI Bulletin No. 203, pp. 313-317.

Davis, K.B., et al., "Use of RAPD Markers to Investigate the Effects of Pollen Processing and Pollen Storage on Pollen Vigor," *Proceedings of the 24th Biennial Southern Forest Tree Improvement Conference*, Orlando, Florida, Jun. 9-12, 1997, p. 405.

Nance, W.L., and C.D. Nelson, "Restriction Fragment Length Polymorphisms and Their Potential Use in Marker Assisted Selection in Southern Pine Improvement," *Proceedings of the 20th Southern Forest Tree Improvement Conference*, Charleston, South Carolina, Jun. 26-30, 1989, pp. 50-56.

Neale, D.B., and C.G. Williams, "Restriction Fragment Length Polymorphism Mapping in Conifers and Applications to Forest Genetics and Tree Improvement," *Can. J. For. Res.* 21:545-554, 1999.

Neale, D.B., et al., "Restriction Fragment Length Polymorphism Mapping of Loblolly Pine: Methods, Applications, and Limitations," *Proceedings of the 20th Southern Forest Tree Improvement Conference*, Charleston, South Carolina, Jun. 26-30, 1989, pp. 363-372.

Nesbitt, K.A., et al., "Fingerprinting and Pedigree Analysis in *Eucalyptus globulus* Using RAPDs," *Silvae Genet.*, Apr. 23, 1996, pp. 6-10.

Richardson, T., et al., "Application of DNA Markers in *Pinus radiata*," *Proceedings of IUFRO '97 Genetics of Radiata Pine*, Rotorua, New Zealand, Dec. 1-4, 1997, FRI Bulletin No. 203.

Vaillancourt, R.E., et al., "Fingerprinting for Quality Control in Breeding and Deployment," *Australian Forestry* 61(3):207-210, Apr. 21, 1998.

White, T.L., and G.R. Hodge, "Best Linear Prediction of Breeding Values in a Forest Tree Improvement Program," *Theor. Appl. Genet* 76:219-727, 1988.

Borralho, N.G., et al., *Catalog of Genetic Values for Pinus radiata D. Don* School of Forestry Sciences, University Austral of Chile, Jul. 1996, 8 pp. [translation].

Claros, M.G.D, "Molecular Markers: What They Are, How They Are Obtained and What They Are Used For," 1998 <http://www.ciencias.ua.es/publicationses/encuentros/ENCUENTROS49/marcadores.html> [retrieved Apr. 25, 2002] [translation].

Espejo, J.C., et al., *Manual for Controlled Cross-Breeding of Eucalyptus nitens (Deane et Maiden) Maiden and Eucalyptus globulus (Labill)*, School of Forestry Sciences, University Astral of Chile, 1995 [translation].

Vergara, R.L., et al., *Manual for Controlled Cross-Breeding of Pinus radiata D. Don*, School of Forestry Sciences, University Austral of Chile, 1995 [translation].

Anzidei, M., et al., "Chloroplast Microsatellites for Analysis of the Geographic Distribution of Diversity in Conifer Species," in E.M. Gillet (ed), *Which DNA Marker for Which Purpose?* (Final Compendium of "Development, Optimisation and Validation of Molecular Tools for Assessment of Biodiversity in Forest Trees," European Union DGXII Biotechnology FW IV Research Programme: Molecular Tools for Biodiversity), 1999, <http://webdoc.gwdg.de/ebook/y/1999/whichmarker/m09/Chap9.htm> [retrieved Nov. 18, 2003].

Cervera, M.T., et al., "Application of AFLP™-Based Molecular Markers to Breeding of *Populus* spp.," *Plant Growth Regulation* 20:47-52, 1996.

Edwards, K.J., and R. Mogg, "Plant Genotyping by Analysis of Single Nucleotide Polymorphisms," in R.J. Henry (ed.), *Plant Genotyping: the DNA Fingerprinting of Plants*, CAB International, Oxfordshire, U.K., 2001, pp. 1-13.

Isagi, Y., et al., "Microsatellite Analysis of the Regeneration Process of *Magnolia obovata* Thunb.," *Heredity* 84:143-151, 2000.

Krauss, S.L., and R. Peakall, "An Evaluation of the AFLP Fingerprinting Technique for the Analysis of Paternity in Natural Populations of *Persoonia mollis* (Proteaceae)," *Aust. J. Bot.* 46:533-546, 1998.

Nicese, F.P., et al., "Molecular Characterization and Genetic Relatedness Among Walnut (*Juglans regia* L.) Genotypes Based on RAPD Markers," *Euphytica* 101:199-206, 1998.

Qiagen, "Plant Nucleic Acid Purification: Technical Hints and Applications," Oct. 2000.

Staub, J.E., and F.C. Serquen, "Genetic Markers, Map Construction, and Their Application in Plant Breeding," *HortScience* 31(5):729-740, Sep. 1996.

Hormaza Ji, "Early selection in cherry combining RAPDs with embryo culture," *Sci Horti* 79 pp. 121-126 (1990).

Saar A et al., "Gametophilic competition in pearl millet, Penniseum typhoides (Staph et. Hubb.)," *Genome* 30: pp. 924-929 (1988).

\* cited by examiner

POLLEN POLYMIX PLANT BREEDING METHOD UTILIZING MOLECULAR PEDIGREE ANALYSIS

FIELD OF THE INVENTION

The present invention is directed to a plant breeding and testing method that utilizes a pollen mixture derived from many male parents in conjunction with field trials and molecular pedigree analysis to evaluate breeding values and make progeny selections for the next generation of breeding.

BACKGROUND OF THE INVENTION

For decades, tree breeders have faced the dilemma of how to mate a select group of individuals (parents) for the next generation of genetic improvement (see step 3 of Table 1). Initially, plant breeders have no problem making selections of individual trees that have desired phenotypic traits from progeny tests or commercial tree stands. The difficulty faced by tree breeders is how to design a plant breeding program using the select individuals to accomplish tree improvement through future generations. The chosen mating design is usually a compromise as no single plant breeding design has been found that best meets all of the objectives of a long-term tree breeding program (Namkoong, *U.S.D.A. Forest Service Technical Bulletin* No. 1588:342 (1979)).

TABLE 1

Process flow for a typical genetic improvement program for forest trees.

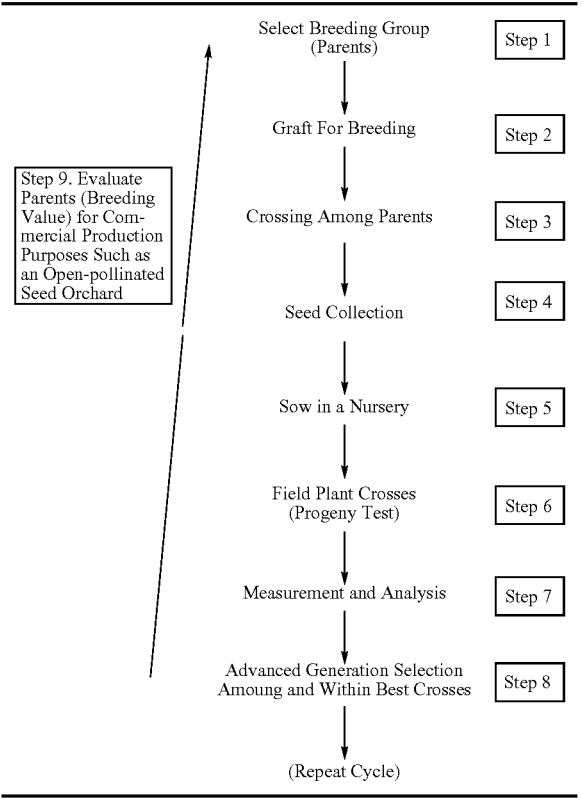

In general, plant breeding designs share the following common objectives:

1. Accurately estimate the breeding value of the parents being bred for purposes of recommending which to include in a production seed orchard or for purposes of determining which crosses to make new selections in for the next generation of breeding, i.e., those crosses between high breeding value parents. This selection of parents based on progeny performance is also called "backward" selection. See step 9, Table 1.
2. Produce a set of crosses that will allow high genetic gain potential from selection of the best individuals within the best crosses for the next generation of breeding, often called "forward" selection. See step 8, Table 1.
3. Allow full pedigree control where both male and female parents are known for new selections in order to control the level of inbreeding.
4. Generate sound estimates of genetic parameters in field trials such as heritability, general and specific combining ability, genetic correlations among traits and genotype-environment interaction.
5. Do all of the above efficiently in order to keep breeding and testing costs at an acceptable level.

The most obvious breeding scheme to achieve all of the above objectives would be to cross every parent with every other parent (full diallel cross) but that alternative is almost always rejected in operational breeding improvement programs due to the fact that it is impractical to make and test so many crosses. The number of total selections may be on the order of a few hundred trees and the number of possible crosses is in the thousands, a number that may be prohibitively expensive to breed and test. The latter is especially true for tree species which, due to their large size, require special equipment to do breeding and a large area for testing individual plants. Consequently, forest geneticists have sought other mating and testing designs that achieve their primary objectives as efficiently as possible.

Mating designs that have been commonly compared in the literature are open pollination versus controlled pollination and, for the latter, full-sib crossing versus polymix (a mixture of pollen from several males) crossing (Bridgwater, In: Fins et al. (eds.) *Handbook of Quantitative Forest Genetics*, Kluwer Academic, Dordrect, The Netherlands, pp. 140-194 (1992)). The most common method of quantitative comparisons of these mating designs in the literature is to hold the number of parents bred and number of progeny tested from crosses among them as constants in each generation of breeding and then determine how well each design estimates genetic parameters and their genetic gain potential. A synopsis of these comparisons of breeding methods follows.

Open Pollination

Open pollination (OP) in forestry is usually assumed to take place in a progeny test where only a hand full of new selections are found among several hundred or a few thousand other individuals. OP breeding gives good estimation of parental breeding values and heritability estimates (Bridgwater, In: Fins et al. (eds.) *Handbook of Quantitative Forest Genetics*, Kluwer Academic Pub., Dordrect, The Netherlands. pp. 140-194 (1992); Cotterill, *Proc. IUFRO Conference on Breeding Theory, Progeny Testing and Seed Orchards*, Williamsburg, Va., USA., pp. 144-149 (1986); Cotterill, *Silv. Genet.* 35(5-6):212-223 (1986b); White, In: *Proc QFRI-IUFRO Conf, Tree Improvement for Sustainable Tropical Forestry*, Caloundra, Australia, pp. 110-117 (1996)).

The genetic gain potential from using the OP families for the next generation of progeny testing is weak since the select parents are mated with a nonselect population from the previous generation (Cotterill, *Proc. IUFRO Conference* on *Breeding Theory, Progeny Testing and Seed Orchards*, Williamsburg, Va., USA., pp. 144-149 (1986a); Cotterill, *Silv. Genet.* 35(5-6):212-223 (1986); van Buijtenen et al., In: *Proc IUFRO Joint Meeting of Genetic Working Parties on Advanced Generation Breeding*, Bordeaux, France, pp. 11-29 (1976)). This and other disadvantages such as lack of full pedigree control and the inability to estimate specific combining ability have resulted in limited use of OP breeding in forestry except in programs where limited resources dictate a simple and low cost approach.

Full-Sib Crossing

There are many mating patterns that have been discussed and analyzed in the literature including full-diallel, cousin mating, single-pair, nested, factorial, disconnected half-diallels and circular systems (Bridgwater, In: Fins et al. (eds.). *Handbook of Quantitative Forest Genetics*, Kluwer Academic Pub., Dordrect, The Netherlands. pp. 140-194 (1992); Burdon and van Buijtenen, *Can. J. For. Res.* 20:1664-1671 (1990); Cotterill, *Proc. IUFRO Conference on Breeding Theory, Progeny Testing and Seed Orchards*, Williamsburg, Va., USA., pp. 144-149 (1986); Cotterill, *Silv. Genet.* 35(5-6):212-223 (1986); Huber et al., *For. Sci.* 38(4):757-776 (1992); Pederson, *Theor. Appl. Genet.* 42:371-377 (1972); van Buijtenen and Burdon, *Can. J. For. Res.* 20:1648-1663 (1990)). Of these, the last three have been commonly used in forest tree improvement because they provide several strengths including reasonably good parameter estimation (general and specific combining ability, heritability, breeding value of parents), provide a foundation for reasonably good genetic gain and provide full pedigree control. In these designs each parent is usually mated to four to six of the other parents in the breeding group.

The weaknesses of the full-sib systems are the amount of work involved in breeding and testing and the fact that they are not the best designs for estimating breeding value nor do they provide the best foundation for selection for the next generation of breeding. These limitations stem from the relatively few crosses for each parent. For a given population size for the progeny test of the crosses it is generally better to have many crosses per parent for precise parameter estimation and high genetic gain potential from forward selection (Pederson, *Theor. Appl. Genet.* 42:371-377 (1972); White, In: *Proc QFRI-IUFRO Conf, Tree Improvement for Sustainable Tropical Forestry*, Caloundra, Australia, pp. 110-117 (1996)) especially when selection emphasis is heavily on family versus individual within family under low heritability situations. Performance of a small number of crosses can result in inaccurate breeding value estimation, especially if there is significant specific combining ability (SCA) in the breeding population (Burdon and van Buijtenen, *Can. J. For. Res.* 20:1664-1671 (1990); van Buijtenen and Burdon, *Can. J. For. Res.* 20:1648-1663 (1990)). Genetic gain for the next generation is limited due to the fact that the best parents, among those being bred, may not have been frequently mated to the other best parents due to chance. Nonetheless, few crosses and many individuals per cross are usually opted due to the high cost of making and testing the crosses. Although full pedigree is known, the limited number of crosses usually means that there is a tendency to select from within a few good crosses. However, there are limitations in so doing because there can often be common parentage among those crosses such that inbreeding concerns force selection from mediocre families, thus limiting genetic gain.

Polymix Crossing

Polymix crossing is done by mixing pollen from several males and applying the pollen to isolated females. One of the advantages to polymix crossing is the simplicity of crossing and subsequent testing of relatively few crosses. Polymix crossing is sometimes considered for parental breeding value (BV) estimation only (Burdon and van Buijtenen, *Can. J. For. Res.* 20:1664-1671 (1990); White, In: *Proc QFRI-IUFRO Conf, Tree Improvement for Sustainable Tropical Forestry*, Caloundra, Australia, pp. 110-117 (1996)), in which case the source of pollen may or may not be made up of the parents in the breeding group, or as a complete breeding system for BV estimation and as a foundation for selection of individuals for advanced generation breeding. In the latter case it is preferable to use pollen from the select group in order to keep genetic gain potential high (Cotterill, *Proc. IUFRO Conference on Breeding Theory, Progeny Testing and Seed Orchards*, Williamsburg, Va., USA., pp. 144-149 (1986); Cotterill, *Silv. Genet.* 35(5-6):212-223 (1986); Burdon and Shelbourne, *NZ J. For. Sci.* 1(2):174-193 (1971); Kerr, *Theor. Appl. Genet.* 96:484-493 (1998); Shelbourne, Tech Pap. No. 55, New Zealand Forest Service, 44 pp. (1969)). PMX crossing provides excellent estimation of breeding value and general combining ability (GCA), but not usually specific combining ability (SCA) (Bridgwater, In: Fins et al. (eds.). *Handbook of Quantitative Forest Genetics*, Kluwer Academic Pub., Dordrect, The Netherlands. pp. 140-194 (1992); Huber et al., *For. Sci.* 38(4):757-776 (1992)). However, Janssens (*Silv. Gen.* 29(3-4):138-140 (1980)) devised a nested PMX design that allows for estimation of SCA variance at the population level but obviously does not estimate SCA effects for a specific cross. Genetic gain potential for forward selection is good but not as high as that offered by the commonly used full-sib systems mentioned above. The gain potential from PMX crossing is 70% to over 90% of the potential for full-sib systems (Cotterill, *Proc. IUFRO Conference on Breeding Theory, Progeny Testing and Seed Orchards*, Williamsburg, Va., USA., pp. 144-149 (1986); Cotterill, *Silv. Genet.* 35(5-6):212-223 (1986); Kerr, *Theor. Appl. Genet.* 96:484-493 (1998); Shelbourne, Tech Pap. No. 55, New Zealand Forest Service, 44 pp. (1969); van Buijtenen and Burdon, *Can. J. For. Res.* 20:1648-1663 (1990)), depending on the magnitude of genetic parameters, with increasing heritability and SCA favoring PMX crossing (van Buijtenen and Burdon, *Can. J. For. Res.* 20:1648-1663 (1990)).

The primary reason that PMX systems result in less genetic gain from advanced generation selections versus full-sib systems is due to the fact that the paternal parent's GCA is unknown. When individual selections are made within the best full-sib crosses for the next generation of breeding they are commonly chosen on the basis of an index that includes the following information:

$$\text{Individual Breeding Value} = \text{female } GCA + \text{male } GCA + h^2_w(\text{individual deviation within the full-sib cross}) \quad (1)$$

Where: $h^2_w$=within cross heritability.

For the PMX cross individual value is estimated as follows:

$$\text{Individual Breeding Value} = \text{female } GCA + h^2_w(\text{individual deviation within the } PMX \text{ cross}) \quad (2)$$

Selection within PMX crosses does not have the benefit of knowing the male GCA, but the heritability for and variation within a PMX crossing scheme is greater than that for full-sib crosses due to the fact that a PMX cross is actually made up of the variation among many full-sib crosses as well as the variation within those crosses. In balance, lack of information on male GCA results in the somewhat reduced gain efficiency of PMX breeding and testing systems mentioned above. Lack of full pedigree control and the possibility that a few males may be represented among selections for the next generation breeding resulting in possible inbreeding depression is another drawback that has limited use of PMX crossing as a stand alone system (Bridgwater, In: Fins et al. (eds.). *Handbook of Quantitative Forest Genetics*, Kluwer Academic Pub., Dordrect, The Netherlands. pp. 140-194 (1992)).

Combined Systems

Many plant breeders have gone to a combination of mating designs in order to take advantages of the strengths of each and to offset, to some degree, the limitations of any one design (van Buijtenen and Burdon, *Can. J. For. Res.* 20:1648-1663 (1990)). The major tree improvement cooperatives for pine species in the southeastern U.S. have gone to a complementary system consisting of PMX crossing for parental breeding values and full-sib crossing from which selections are made for the next generation of breeding (Lowe and van Buijtenen, In: *Proc IUFRO Conf on Breeding and Testing Theory, Progeny Testing and Seed Orchards*, Williamsburg, Va., pp. 98-106 (1986); McKeand and Bridgwater, In: *Proc IUFRO Resolving Tropical Forest Resource Concerns Through Tree Improvement, Gene Conservation, and Domestication of New Species*, Cali, Colombia, pp. 234-240 (1992); White et al., *Silv. Genet.* 42:359-371 (1993)). Full-sib crossing is typically a circular or disconnected half diallels design. While offering many advantages, these systems are costly of time and resources. Furthermore, they do not overcome the limitation of few crosses per parent and the fact that the best parents may not often be mated with the other best parents, thus limiting gain from selection with crosses and/or creating relatedness limitations among advanced generation selections.

In summary, the type of plant breeding strategy selected for use in a plant breeding program depends upon a number of different factors. However, a common goal of a plant breeding program is to generally use a breeding method that will result in the largest possible genetic gain using the smallest number of breeding crosses and the least amount of time and money. What is needed in the art of plant breeding is a breeding method that will reduce the number of generations that are required in a plant breeding program to achieve an improved plant variety yet at the same time be cost and time effective.

The present invention provides a new plant breeding method that utilizes cost and time effective parental pedigree determination using molecular analysis in conjunction with phenotypic scores to efficiently select elite progeny plants for use in the next generation of plant breeding. The molecular pedigree methods used in the present invention overcome the heretofore primary limitations of PMX breeding and testing which are lack of male pedigree control and lack of male GCA information for advanced generation selection. More specifically, the present invention provides a plant breeding design which utilizes PMX crosses in conjunction with molecular marker technology to determine pedigree. Given a sufficient number of reliable, polymorphic molecular markers, and modest care in creation of pollen polymixes, paternity of all PMX progeny can be unambiguously determined through molecular analysis. Therefore, the present invention provides a plant breeding method that allows for pedigree control and estimation of breeding values of the parental plants and their progeny.

SUMMARY OF THE INVENTION

In one aspect, the present invention provides a plant breeding method having the following steps:

(a) Mixing pollen from a breeding group comprised of a plurality of parental plants to obtain a pollen polymix;
(b) Pollinating a female reproductive structure from each parental plant in the plurality of parental plants with the pollen polymix to obtain a plurality of progeny lots wherein each progeny lot comprises seeds obtained from a different cross between the pollen polymix and each different parental plant of the plurality of parental plants;
(c) Evaluating progeny plants grown from each of the progeny lots using objective criteria to obtain a phenotype score;
(d) Determining the pedigree of the progeny plants using molecular parental analysis; and
(e) Using the pedigree and phenotype score to identify elite plants for use in a next generation of plant breeding.

In one embodiment of the present invention, the method contains the additional step of selecting candidate plants from within the progeny plants grown from each of the progeny lots based upon phenotype score. In this embodiment, molecular parental analysis is performed on the candidate plants rather than all of the progeny plants. Elite plants are identified based upon the pedigree and phenotype scores of the candidate plants.

In another embodiment of the invention, the female pedigree (maternity) of the polymix progeny plants is known and the molecular parental analysis is used to determine the male pedigree (paternity) of the progeny plants based upon a molecular parental analysis of all potential male parents (i.e. those parents who contributed pollen to the pollen polymix). In yet another embodiment of the invention, the male and female pedigree of the progeny plants is unknown and the molecular parental analysis is used to determine the male and female pedigree of the progeny plants based upon the molecular analysis of potential male and female parents.

In other embodiments of the invention, the phenotype score is obtained for a plant phenotype selected from the group consisting of disease resistance, growth rate, growth habit, chemical composition of any plant tissue, drought resistance, temperature hardiness, elevation adaptation, fecundity, breeding values for these phenotypic scores, and any combination thereof.

In still other embodiments of the invention, the molecular parental analysis is performed using a method selected from the group consisting of genomic DNA analysis, messenger RNA analysis or analysis of cDNAs derived from the messenger RNA, protein analysis, and any combination thereof.

DNA analysis can be performed using a DNA analysis method selected from the group of DNA sequencing, restriction fragment length polymorphism (RFLP), amplified fragment length polymorphism (AFLP), randomly amplified polymorphic DNA (RAPD), single nucleotide repeat microsatellites (i.e., simple sequence repeats (SSR)), di-, tri-, and tetra-nucleotide repeat SSRs, SSR-anchored PCR, sequenced tagged sites (STS), single nucleotide polymorphism (SNP), single stranded conformational polymorphism (SSCP), sequenced characterized amplified regions (SCAR), allele-specific associated primers (ASAP), single primer amplification reaction (SPARs), and cleaved amplified polymorphic sequences (CAP).

Preferably, elite plants are selected from the progeny plants based upon a characteristic selected from the group consisting of phenotype score, estimated breeding value, paternal breeding value, maternal breeding value and any combination thereof.

The present invention also provides a method of evaluating plant progeny resulting from a pollen polymix cross comprising:

(a) evaluating progeny plants grown from a plurality of progeny seed lots obtained from a pollen polymix crossed to a plurality of parental plants using objective criteria to obtain a phenotype score;

(b) determining the pedigree of the progeny plants using molecular parental analysis;

(c) estimating the breeding value of the progeny plants using pedigree and at least one plant phenotype; and (d) using the breeding value to identify elite plants for use in a next generation of plant breeding.

Plant progeny obtained from a pollen polymix cross can also be evaluated using the above method and the additional step of selecting candidate plants from within the progeny lots based upon their estimated breeding value, wherein step (b) is performed on candidate plants which are identified based upon their phenotype score.

The inventive methods can also be performed with progeny plants obtained from pollen polymix crosses performed with a plurality of pollen polymixes. In this embodiment, each pollen polymix is comprised of pollen obtained from a plurality of different parental plants. In order to minimize inbreeding, each pollen polymix is then used to pollinate female reproductive structures from parental plants whose pollen is not represented in the pollinating pollen polymix.

DETAILED DESCRIPTION OF THE INVENTION

As used herein the term "breeding group" refers to a plurality of plants that have been selected based upon at least one desired phenotypic trait that can be measured using objective criteria. Typically this group will be interbred and the resultant progeny tested and used for making selections for future generations of breeding and testing.

The term "objective criteria" is meant to include the measurement of any plant characteristic or phenotype with any detection/measurement device that provides statistically meaningful data regarding the characteristic or phenotype being measured.

The term "phenotype score" as used herein refers to the objective measurement of any phenotypic trait or characteristic that is desirable in a plant breeding program. Examples of desired phenotypic traits or characteristics include disease resistance, growth rate, growth habit, chemical composition of any plant tissue, drought resistance, temperature hardiness, elevation adaptation, fecundity and so on.

The term "breeding value" as used herein refers to any measure of plant desirability that relates to plant breeding. The breeding value (BV) of a plant is determined by its general combining ability when mated to other parents in a breeding group. BV is based on a statistical analysis of progeny test data that minimizes environmental bias from the estimate of an individuals true genetic worth. BV is the value of an individual for breeding purposes. In its simplest form, BV of a parent is twice the deviation of its progeny mean over the test mean of all progeny when the parent is mated to a random sample of other parents. The deviation of the progeny mean from the overall mean is also known as GCA. An individual progeny's breeding value is the sum of the GCAs of the parents and the product of its deviation from the progeny lot mean times heritability. Breeding value may be based upon a single desirable phenotypic trait or any combination of phenotypic traits that are of importance in a plant breeding program.

The term "pollen polymix" or "PMX" as used herein refers to a mixture of pollen that was obtained from a plurality of pollen donors having different genotypes. Usually a pollen polymix is made by obtaining pollen from each plant that is being used to obtain an advanced generation of plants from a breeding line composed of a plurality of plants having at least one desired phenotypic trait. However, the term also includes pollen polymixes designed to minimize inbreeding by exclusion of pollen within the polymix from the parental plant being pollinated. Pollen polymixes may also be designed to exclude a parental plant pollen donor because the molecular analysis being used to determine pedigree cannot sufficiently distinguish between two or more of the parental plants to assign parentage to the pollen polymix progeny.

The term "female reproductive structure" as used herein refers to any plant tissue that is receptive to pollen and facilitates pollen germination and fertilization of a female gamete. Exemplary female reproductive structures include, but are not limited to angiosperm gynoecium, such as found on monoecious plants having imperfect flowers (pistils only), or on dioecious plants having perfect flowers (pistils and stamens), and gymnosperm pistillate strobili.

The term "progeny lot" as used herein refers to a collection of seeds obtained from a cross between a pollen polymix and female reproductive structures of one of the parental plants in the breeding group. All of the seeds in one progeny lot have one maternal parent.

The term "pedigree" as used herein refers to the maternal or paternal sources of genetic material that gave rise to a particular progeny plant. Pedigree can refer to determination of an individual's parents, grandparents, siblings and so on.

The term "candidate plant" as used herein refers to a plant that has at least one desirable phenotypic trait that makes that plant more desirable than other plants from the same generation.

The term "molecular parental analysis" or "molecular analysis" as used herein refers to the use of any method that analyzes the molecular components of a plant for the purpose of determining the plants pedigree. Molecular methods useful in the practice of the present invention allow the determination or inference of an individual's genotype based upon analysis of that individual's chemical constituents. The genotype information is then compared to all potential parent genotype information to infer the pedigree of the individual. Typical molecular methods that can be used in the practice of the invention include, but are not limited to, genomic DNA analysis, messenger RNA analysis, analysis of cDNA derived from messenger RNA, protein analysis, secondary compound analysis, i.e., cell wall components, flavonoles, monoterpenes, etc., and any combination thereof.

The term "DNA analysis" as used herein refers to any method of DNA analysis that reveals genotype information. Genotype information may be obtained from any one of the genomic DNAs of a target organism, such as for example, a nuclear genome, a mitochondrial genome, a chloroplast genome or any combination thereof. Examples of the types of DNA analysis include, but are not limited to, DNA sequencing, restriction fragment length polymorphism (RFLP), amplified fragment length polymorphism (AFLP), randomly amplified polymorphic DNA (RAPD), single nucleotide repeat microsatellites (i.e., simple sequence repeats (SSR)), di-, tri-, and tetra-nucleotide repeat SSRs, SSR-anchored PCR, sequenced tagged sites (STS), single nucleotide polymorphism (SNP), single stranded conformational polymorphism (SSCP), sequenced characterized amplified regions (SCAR), allele-specific associated primers (ASAP), single primer amplification reaction (SPARs), cleaved amplified polymorphic sequences (CAP), and any other analytical technique that reveals DNA sequence polymorphisms.

The plant breeding method of the present invention can be used in plant breeding programs for almost any plant species of agricultural or horticultural value. The only plant requirement for practice of the invention is that the selected plant species be amenable to pollen polymix pollination wherein the polymix pollination results in the production of full sib families. This condition may be met by performing a polymix pollination on one or more female reproductive structures so long as the female gametes being fertilized by the pollen polymix are derived from a parent plant having the same genotype. The inventive methods include both dioecious and monoecious plants that meet the above criteria.

The collection and storage of plant pollen is well known in the art as are methods for determining the fertility of the pollen collected from each plant that is a member of the breeding group (for tree species, see for example, Advances in Pollen Management, *U.S.D.A. Forest Service Agriculture Handbook No.* 698:1-101 (1993)). In general, pollen from several of the parents in the breeding group is mixed using pollen management processes that are known for the particular species being breed. Pollen from different parents can be mixed proportionally by volume or weight or by some determination of the viable number of pollen grains per volume or weight. There may be one or more pollen mixes used in the practice of the present invention. For example, more than one pollen polymix may be used for better pedigree control to reduce inbreeding or to prevent ambiguity in DNA paternity analysis due to two or more parents being closely related.

The seeds resulting from each flower pollination are collected into progeny lots. The seeds in each progeny lot have the same female parent. Usually the pedigree of the female parent of the seeds within each individual progeny lot is known. In other embodiments of the present invention the female parent of the seeds is not recorded and both female and male pedigree is determined by DNA analysis.

Progeny plants are grown from seeds from each progeny lot and a desired phenotypic trait of the progeny plant is objectively measured to obtain a phenotype score. Examples of plant phenotypic traits that are commonly assayed include disease resistance, herbicide resistance, growth rate, growth habit, agricultural yield, chemical composition, drought resistance, temperature and elevation adaptation, and so on. A phenotypic score is objectively measured when the methodology employed to obtain a phenotypic score yields statistically meaningful results using any one of many well known statistical computer programs. In addition, computer software is also available for statistical analysis of breeding values and heritability determinations, such as GAREML (Dr. Dudley Huber, University of Florida, Gainsville, Fla.).

Candidate plants are identified from the progeny plants based upon at least one objectively measured phenotypic trait. Those plants that have at least one phenotypic characteristic that is statistically better, based upon the objective criteria, than other progeny plants obtained from within the progeny test may be designated as candidate plants. The number of candidate plants selected for molecular pedigree evaluation depends upon the financial and time resources available to the plant breeder and the ultimate goal of the breeding program.

The pedigree of a plant is performed using any molecular analysis method that allows the determination or inference of an individual's genotype based upon analysis of that individual's chemical constituents. The resulting genotype information is then compared to all potential parent genotype information to infer the pedigree of the individual. Typical molecular methods that can be used in the practice of the invention include, but are not limited to, genomic DNA analysis, messenger RNA analysis, analysis of cDNA derived from messenger RNA, protein analysis, secondary compound analysis and any combination thereof.

Any molecular analysis method can be used that reveals a sufficient number of genetic polymorphisms to identify which parental plants used in the original breeding crosses are the likely parents of any one of the candidate plants being tested. The ability to accurately assign parentage and estimate relatedness using molecular methods depends on many different factors, such as:

Size of the potential parent pool or parental combinations;
Amount of relatedness among parents;
Prior knowledge of parental genotypes (one parent known vs. no parental genotypes);
Type of marker chosen (information content, number of loci, repeatability, inheritance i.e., Mendelian, paternal, maternal);
Population gene frequencies;
Statistical models (exclusion vs. likelihood paternity or maternity assignments); and
Genotype error and mutation rates.

The above noted factors are well known in the art of paternity DNA analysis (see for example, humans (Hohoff and Brinkmann, *Mol. Biotech.* 13:123-136 (1999)); *Drosophila*, (Dewoody et al. *Genet. Res. Camb.* 75:95-105 (2000)); salmon (Norris et al., *Aquaculture* 182:73-83 (2000)), shrubs (Krauss, *Mol. Ecol.* 8:217-226 (1999)) and trees (Isagi et al., *Heredity* 84:143-151 (2000)). Additionally, the cost of genotyping will significantly influence how the technique is applied.

DNA analysis is most typically performed on total genomic DNA extracted from a plant tissue sample. Such a DNA sample includes sequences from the nuclear, mitochondrial and cholorplast genomes of the plant. Alternatively, when desirable, nuclear, mitochondrial and cholorplast DNA sequences can be individually enriched during DNA isolation from the plant tissue using methods that are well known in the art. In addition, a wide variety of DNA extraction and purification methods have been developed in the art for preparing plant DNA samples from a wide variety of plant tissues and different plant species. Paternity analysis of plants can also be performed by analysis of cDNA prepared from RNA samples extracted from a plant tissue. Most usually a polymerase chain reaction (PCR) procedure is used to amplify specific cDNA sequences for detection of genetic polymorphisms. For example, a difference in the mobility of a PCR amplified cDNA fragment is indicative of a genetic polymorphism.

Analysis of protein patterns using, for example, electrophoretic techniques may also be used to determine plant paternity (see generally, Nakamura and Wheeler, *Evolution* 46(3):846-851 (1992); Wheeler and Jech, *New Forests*, 6:311-328 (1992); Advances in Pollen Management, *U.S.D.A. Forest Service Agriculture Handbook* No. 698:55-63 (1993) and references disclosed therein). In addition, monoterpene profiles, and other secondary compounds, can be used to obtain paternity information (see for example, Advances in Pollen Management, *U.S.D.A. Forest Service Agriculture Handbook* No. 698:55 (1993)).

DNA marker applications in tree improvement and tree breeding have increased notably in recent years, including such uses as clonal fingerprinting for identification and taxonomic analysis, creation of genetic maps, dissection of complex traits and quantitative trait loci detection, and marker-aided selection (Groover et al., *Genetics* 138:1293-1300 (1994); O'Malley and McKeand, *For. Gen.* 1:207-218 (1994); O'Malley et al., In: *Genomes of Plants and Animals: 21st Stadler Genetics Symposium*, Gustafson and Flavell (eds.). Plenum Press, New York (1996); Staub et al., *HortScience* 31:729-740 (1996); Cervera et al., *Plant Growth Regulation* 20:47-52 (1996); Dinus and Tuskan, In: *Micropropagation, genetic engineering and molecular biology of Populus*, Ed., Klopfenstein et al. USFS Gen. Tech. Rep. RM-GTR-297. p. 220-235 (1997)). However, genetic marker applications focused on pedigree issues in forestry are largely restricted to seed orchard studies, including estimating pollen contamination, measuring self-pollination verse out-crossing rates, male reproductive success, and supplemental mass pollination success (Wheeler and Jech, *New Forest* 6:311-328 (1992); Stoehr et al., *Can. J. For. Res.* 28:187-195 (1998)). Most orchard applications rely on paternity analysis to infer pollen donors. Paternity analyses have also been applied in natural stand progeny arrays (Ziegenhagen et al., *Can. J. For. Res.* 28: 317-321 (1998)).

More recently, rapid advancement in the development of highly informative markers has led to increased use of pedigree analyses for parentage assignment and estimation of relatedness among progeny arrays for a number of species including humans (Hohoff and Brinkmann, *Mol. Biotech.* 13:123-136 (1999)); *Drosophila*, (Dewoody et al. *Genet. Res. Camb.* 75:95-105 (2000)); salmon (Norris et al., *Aquaculture* 182:73-83 (2000)), shrubs (Krauss, *Mol. Ecol.* 8:217-226 (1999)) and trees (Isagi et al., *Heredity* 84:143-151 (2000)).

Examples of the types of DNA analysis include, but are not limited to, DNA sequencing, restriction fragment length polymorphism (RFLP), amplified fragment length polymorphism (AFLP), randomly amplified polymorphic DNA (RAPD), single nucleotide repeat microsatellites (i.e., simple sequence repeats (SSR)), di-, tri-, and tetra-nucleotide repeat SSRs, SSR-anchored PCR, sequenced tagged sites (STS), single nucleotide polymorphism (SNP), single stranded conformational polymorphism (SSCP), sequenced characterized amplified regions (SCAR), allele-specific associated primers (ASAP), single primer amplification reaction (SPARs), and cleaved amplified polymorphic sequences (CAP) (Mueller and Wolfenbarger, *TREE* 14:389-394 (1999); Staub et al., *HortScience* 31:729-740 (1996); Morell et al., *Australian J. of Exp. Agri.* 35:807-819 (1995)).

Once the pedigree and phenotype scores have been determined for the selected candidate plants then the breeding values of the candidate plants can be estimated and used to make the final selection of elite plants for use in the next generation of plant breeding. For example, an elite plant that has a high phenotype score and has parents that are of high breeding value is particularly valuable as a breeding parent in the next generation. Further, knowledge of an elite plant's pedigree allows selection of the next generation of parental plants to maximize the genetic diversity of new breeding groups.

In one embodiment of the present invention a set of plants are provisionally identified as candidate plants for use in advanced generation breeding (step 8 in Table 1) using female GCA and objective measurements of individual phenotype performance (phenotype score) as selection criteria. Tissue samples are obtained from all of the parental plants used in PMX crosses and from a subset of selected progeny plants, which are designated as "candidate plants", based upon their phenotype score. The paternity of the tissue samples from the candidate plants are obtained using molecular analysis by comparison to the tissue samples obtained from each parental plant in the breeding group. Elite plants are selected by determining that the fathers of the candidate plants have an acceptable GCA and an acceptable level of relatedness based on some criteria such as group merit which weighs genetic gain potential against an estimate of inbreeding depression (Rosvall and Andersson, *For. Gen.* 6(1):1-14 (1999)). One limitation of this method is that the initial selection of the plants in the breeding line may not include the highest value individuals available for inclusion in the PMX crosses since male GCA is not known when the candidate plants are selected. Nonetheless, the final screening based on paternity analysis should allow genetic gain higher than had been possible with PMX crossing systems in the past. This system may be chosen for tree species when, e.g., paternal analysis cost per individual is somewhat expensive such as about $30 to $50 per individual.

In a second embodiment of the invention, genetic typing of all original parents and paternal analysis (based on genetic markers) for all individuals destined for field testing is carried out either in the nursery (step 5) or in the field test (step 7) at the time of phenotype measurement (see Table 1). By determining the father of all individuals before determination of phenotype score, the information on both male and female parentage can be used in advanced statistical analysis and in advanced generation selection as is done in any other full-sib mating system. Besides the usual advantages of PMX breeding, this system has several advantages over other full-sib systems such as the commonly used circular and disconnected half diallels (Bridgwater, In: Fins et al. (eds.) *Handbook of Quantitative Forest Genetics*, Kluwer Academic Pub., Dordrect, The Netherlands. pp. 140-194 (1992); White, In: *Proc QFRI-IUFRO Conf, Tree Improvement for Sustainable Tropical Forestry*, Caloundra, Australia, pp. 110-117 (1996)). As long as fertilization is mostly at random, many effective crosses are generated with PMX mating resulting in greater genetic gain potential for advanced generation selection and more flexibility for relatedness control. Also, genetic typing of all individuals helps reduce the number of identity (pedigree) errors that are carried into future generations, a serious concern in any genetic improvement program (Adams et al., *Silva. Genet.* 37:147-152 (1988); Ericsson, *Silva. Genet.* 48:239-242 (1999)). This scenario is possible when molecular analysis is cheap enough to genetically type all individuals, e.g., about $3 to $5 per individual for many tree species.

In yet another embodiment of the invention, after the progeny seed is processed (step 4, Table 1) equal (or known) quantities of seed from the PMX crosses are completely mixed before sowing in the nursery. The nursery crop and the field test are established without PMX cross identification tags. That is, the female heritage identity of progeny plants is not recorded. Consequently, the field test is a completely randomized design. At the time that field measurement of plant phenotype is scored, tissue samples are also taken from all individual progeny and the original parents for molecular analysis of pedigree. The molecular analysis of the parents and progeny plants allows determination of the maternal and paternal parents for all progeny from the PMX cross. This embodiment of the invention is preferred when both maternity and paternity determinations are possible and genetic typing is cheap, e.g., about $3 to $5 per individual in tree species, and when the cost of maintaining identity of crosses in the nursery and/or field test is difficult and/or expensive.

Paternity Assignment Using Molecular Analysis

The ability to assign paternity unambiguously to offspring is the core requirement for the successful adoption of some embodiments of the present invention. In the practice of the present invention, many different statistical approaches to the assigning paternity may be used. For example, genetic exclusion analysis (Smouse and Meagher, *Genetics* 136: 313-332 (1994)) and likelihood models (Marshall et al., *Mol. Ecol.* 7:639-655 (1998); Goodnight and Queller, *Mol. Ecol.* 8:1231-1234 (1999)) may both be used in the practice of the present invention, as well as any other statistical method that infers pedigree from genomic DNA, cDNA, protein, or any other biochemical analyses that produces information that is indicative of the genotype of the individual being tested. The discussion below is illustrative of considerations for using genetic exclusion analysis and likelihood model analysis to determine pedigree using DNA markers. Similar considerations must be weighed when determining pedigree using cDNA, protein or other biochemical fingerprinting methods to obtain genotype information from which pedigree can be inferred.

Genetic Exclusion

Exclusion, where technically and economically feasible, would be desirable in breeding populations where tracking of pedigree and level of inbreeding are critical. Based on the results of the select population studied here (see Examples 4 and 5), it may not be possible to distinguish between all individuals in a test of paternity, largely as a result of the considerable relatedness of the individuals. Complete exclusion of progeny derived from a polymix breeding program as used in the present invention may be obtained using any one of the following strategies:

1) Increase the number of chloroplast DNA markers. For example, in the results presented in Example 4, Table 2, the addition of one or more hypervariable chloroplast sequence tagged site markers (Stoehr et al., *Can. J. For. Res.* 28:187-195 (1998)) would have virtually eliminated the opportunity for unrelated individuals to share haplotypes.

2) Increase the number of nuclear DNA markers. A small increase in the number of microsatellites or alternative markers such as single nucleotide polymorphism markers (SNPs) (Krawczak, *Electrophoresis* 20:1676-1681 (1999); Chakraborty et al., *Electrophoresis* 20:1682-1696 (1999)) or amplified fragment length polymorphism markers (AFLPs) (Mueller and Wolfenbarger, *TREE* 14:389-394 (1999); Krauss, *Mol. Ecol.* 8:217-226 (1999)) would separate unrelated individuals; a larger increase in the number of different markers would be necessary to distinguish between related individuals. Gerber et al. (In: *Which DNA marker for which purpose*. Final Compendium of the Research Project "Development, optimisation and validation of molecular tools for assessment of biodiversity in forest trees" in the European Union DGXII Biotechnology FW IV Research Programme Molecular Tools for Biodiversity. Gillet, E. M. (ed.) (1999)) showed that 4-6 highly polymorphic nuclear simple sequence repeat markers (SSR's), such as those used in Example 4, were sufficient to produce paternal exclusion of 99.9% in a natural population of oak. Approximately 45 AFLP or SNPs loci, with low frequency of "presence" alleles provide similar exclusion probabilities (Chakraborty et al., *Electrophoresis* 20:1682-1696 (1999); Gerber et al. In: *Which DNA marker for which purpose*. Final Compendium of the Research Project "Development, optimisation and validation of molecular tools for assessment of biodiversity in forest trees" in the European Union DGXII Biotechnology FW IV Research Programme Molecular Tools for Biodiversity. Gillet, E. M. (ed.) (1999)). Since first-order relatives always share at least one allele at every locus, paternity exclusion of related individuals is dependent on number of loci available, their level of polymorphism, and population substructure.

3) Alternatives to the addition of new markers. Complete paternal exclusion can be insured by eliminating related individuals from the breeding population; or creating polymixes that avoid mixing pollens known to share the same paternal haplotype. In the latter option, related individuals may remain in the population but are used as females only. For the test population used here, assuming haplotype exclusion of all unrelated individuals, six polymixes would be necessary. Additional modeling would be necessary to determine if the reduction in possible mating combinations would adversely affect genetic gain estimates.

Likelihood Models

Likelihood models may be used to statistically assign paternity, parentage, or other levels of relatedness (Marshall et al., *Mol. Ecol.* 7:639-655 (1998); Goodnight and Queller, *Mol. Ecol.* 8:1231-1234 (1999)). However, such models are generally designed to deal with natural populations and assume random mating and non-relatedness. Likelihood approaches may be quite flexible and make full utilization of the data, accounting for such factors as allele frequencies and the potential for genotyping errors or mutations (by modeling double exclusion requirements; Marshall et al., *Mol. Ecol.* 7:639-655 (1998)). Furthermore, paternal assignments may be made with relatively few loci making the approach cost effective. The most significant shortcoming of the likelihood approach is that the probability of assigning paternity incorrectly, given relatedness, can be non-zero. Valuable insight into paternity assignment is provided by Double et al. (*Mol. Ecol.* 6:1155-1166 (1997)). They provide equations for calculating single-locus exclusion probabilities when related males compete for mating, as is the case in our elite populations. They also model exclusion probabilities based on the number of loci used and their level of polymorphism. For instance, to achieve an exclusion probability in excess of 90% when 1, 5 or 10 first order relatives are competing, 5, 8, and 9 loci respectively, each with 10 equally frequent alleles are required. If needed, this would be both technically and economically feasible.

EXAMPLE 1

Preparation of Pollen Polymix 40 elite individuals of loblolly pine were selected in North Carolina progeny tests based on high phenotypic scores and breeding values for growth rate to form a breeding group. These individuals were also above average for straightness and branching habit and were not infected by disease or insects and had no severe stem deformities. These 40 individuals (parents) were grafted onto sexually mature trees for breeding purposes. The graft trees produced separate pistillate (female) and staminate (male) strobili having the genetic characteristics of the original elite trees. Male pollen catkins were collected at about the time of pollen shed from 39 of the elite graft trees and the catkins were dried at around 38 degrees centigrade and around 30% humidity for 48 hours. Under these conditions the pollen has less than 10% moisture content and can withstand freezer storage. Pollen was shaken from the catkins and sifted into airtight bottles for freezer storage until use. A pollen mix from the 39 parents was made up of three cubic centimeters (cc) of pollen per parent except for a few parents that had only one or two cc's of pollen available. This pollen mix was tumbled to ensure complete mixing of the pollen. The amount of pollen per parent in the mix was recorded.

EXAMPLE 2

Polymix Breeding of Pine Trees

A pollen polymix representing 39 male parents was used to pollinate 40 females in a breeding group (see Example 1) whose pistillate strobili were isolated from other pollen in the spring by bagging. Pine cones are collected in the fall, 1.5 years after pollination, and the seed extracted and the identity of the 40 female parents is recorded. The collected seeds correspond to 40 PMX progeny lots. Seeds are stratified and germinated in containers in a greenhouse and planted in progeny tests the following spring. When the progeny test plants reach around four to six years of age the trial trees are measured for height growth, stem diameter growth, straightness, disease resistance, insect resistance, general health and deformities. The growth data is analyzed using a best linear unbiased prediction software called GAREML (Dr. Dudley Huber, University of Florida, Gainsville, Fla.) that generates breeding values for growth rate for the maternal parent and for every individual progeny. The individual progeny breeding value is a function of the maternal GCA and the individuals own growth performance compared to its half siblings. These breeding values and tree quality and disease scores are used to generate a group of trees for inspection in the test of PMX progeny lots. After field inspection a group of 160 candidate selections are made based upon the above calculated breeding values, overall tree quality and pathogen resistance scores. Tissue samples are obtained from each candidate plant as well as the parents that were used to generate the PMX progeny lots. Molecular paternity analysis is performed as described in Examples 3, 4, and 5). The 160 candidate plants are then narrowed down to 40 elite individuals for use in the next generation of breeding and testing based on the father's GCA, considerations of co-ancestry control (relatedness among the selections that may lead to inbreeding concerns), the candidate plant's estimated breeding value and its phenotype score.

EXAMPLE 3

General Methods

Plant Materials For data reported here, needle samples were collected from two groups of trees: 1) 78 first-generation loblolly pine plus-tree selections were used in our analysis to determine gene frequencies for seven chloroplast SSR and three nuclear SSR loci. The first-generation loblolly pine trees were selected in natural stands from North Carolina, South Carolina, and Georgia (Atlantic Coastal Plain provenance, ACP);

2) 45 elite $1^{st}$, $2^{nd}$ and $3^{rd}$ generation loblolly pine selections from Weyerhaeuser's breeding program were used for DNA genotyping at the same suite of chloroplast and nuclear SSR loci. Considerable relatedness was observed among these 45 trees, including half-sibs, full-sibs, parent-offspring, and grand-parent-offspring relationships (See Table 3 in Example 4). Twenty-nine of the 45 trees were identified as being paternally unrelated.

DNA Extraction: DNA was prepared from needle tissue following the CTAB procedure of Doyle and Doyle (*Focus* 12:13-15 (1990)) or using the DNeasy 96 DNA extraction kit (Qiagen, Valencia, Calif.). Briefly, for the CTAB method, 100 mg of needle tissue was placed in a 1.5 mL microfuge tube, frozen with liquid nitrogen, and ground to a fine powder using a plastic pestle. The needle sample was suspended in 700 µL of 2×CTAB buffer, with 200 µg of Proteinase K. The procedure yielded approximately 10 µg. The DNA samples were resuspended in 100 µL of TE buffer (10 mM Tris, 1 mM EDTA, pH8.0). For the DNeasy method, 50 mg of needle tissue was placed in a 2 mL screw cap tube. The tube contained a ceramic ball and cylinder (BIO101, Carlsbad, Calif.). AP1 buffer was added (600 µl) with RNaseA (100 mg/ml, 1.5 µl per sample) and Reagent DX (detergent, 1.5 µl per sample). The samples were homogenized for 45 seconds by agitation (up and down with twisting, at high speed, setting 4.5) in the FastPrep instrument (BIO101, Carlsbad, Calif.). The samples were processed 12 at a time and held on ice until 96 were homogenized. The homogenates were incubated at 65° C. for 30 minutes, then AP2 buffer (protein precipitation, 200 µl) was added and the tubes were shaken for 15 seconds. The tubes were then chilled on ice for 5 minutes before centrifuged 5 minutes at 5600×g. Supernatents (400 µl) were transferred to 96 2 ml tubes (mtp format), then AP3 buffer was added (600 ml) and mixed by pipetting up and down several times. The solutions (~1 ml) were transferred to a DNeasy 96 plate and centrifuged at 5600×g for 4 minutes. AW buffer was added (800 µl) then the plate was centrifuged at 5600×g for 15 minutes. The DNA was eluted from the plate by adding 100 µl of AE buffer, incubating for 1 minute, then centrifuging at 5600×g for 2 minutes. This step was repeated for maximum yield, resulting ~15 to 20 µg of DNA in 200 µl. The concentration of loblolly pine samples was estimated by visual comparison using the fluorescence of ethidium-stained lambda DNA concentration standards on 0.8% agarose gels illuminated with UV-light.

PCR-amplification: DNA fragments were PCR-amplified from loblolly pine genomic DNA samples using the 20 pairs of DNA primers designed by Vendramin et al. (1996) for amplification of chloroplast microsatellite based on the complete DNA sequence of *Pinus thunbergii* (Wakasugi et al., Proc. Nat. Acad. Sci. USA, 91:9794-9798 (1994)). The sense primer was fluorescently labeled with IRD-41. The PCR-reaction was carried out in 5 µl using 40 ng of loblolly pine genomic DNA as template. The PCR reaction protocol (Jang, *Genetic Analysis Bulletin* #30, LI-COR, Inc., Lincoln, Nebr.) used PCR buffer and 1 unit of Taq polymerase (Boehringer Mannheim, 10 mM Tris-HCl, 1.5 mM MgCl2, 50 mM KCl, pH 8.3), 2 pmol reverse (anti-sense) primer, 0.1 pmol IR-labeled forward (sense) primer, 0.1 mM dNTP (using dGTP). The reactions were run in 96-well polycarbonate microtitre plates (25 µL conical-bottom wells). The thermocycler temperature program was [94° C., 30 s; 58° C., 30 s; 72° C., 1 m] repeated 10 times, dropping the annealing temperature by 1 degree each cycle, followed by 23 cycles using the original 58° C. annealing temperature. The stop solution contained 95% formamide, 0.1 mM EDTA, 0.1% bromophenol blue, and 5 µL of stop solution was added to each reaction. Multiplexed PCR reactions contained primer pairs for 4 microsatellites (0.1 pmol of each labeled reverse primer, and 2.0 pmol of each forward primer). Of the 20 primer pairs tested, 7 pairs gave polymorphisms in loblolly pine (Table 2).

TABLE 2

Primer sequences for chloroplast and nuclear microsatellites.

| Primer name and SEQ ID No. | | Primer Sequence |
|---|---|---|
| Chloroplast microsatellites primer pairs | | |
| [2]PT1254f | SEQ ID No. 1 | [1]5'-*CAATTGGAATGAGAACAGA TAGG-3' |
| PT1254r | SEQ ID No. 2 | 5'-TGCGTTGCACTTCGTTATAG-3' |
| PT9383f | SEQ ID No. 3 | 5'-*AGAATAAACTGACGTAGAT GCCA-3' |
| PT9383r | SEQ ID No. 4 | 5'-AATTTTCAATTCCTTTCTTTC TCC-3' |
| PT26081f | SEQ ID No. 5 | 5'-*CCCGTATCCAGATATACTTC CA-3' |
| PT26081r | SEQ ID No. 6 | 5'-TGGTTTGATTCATTCGTT CAT-3' |
| PT30204f | SEQ ID No. 7 | 5'-*TCATAGCGGAAGATCCTC TTT-3' |
| PT30204r | SEQ ID No. 8 | 5'-CGGATTGATCCTAACCAT ACC-3' |
| PT71936f | SEQ ID No. 9 | 5'-*TTCATTGGAAATACACTAG CCC-3' |
| PT71936r | SEQ ID No. 10 | 5'-AAAACCGTACATGAGATT CCC-3' |
| PT109567f | SEQ ID No. 11 | 5'-*TATTATCGAACAACGAGAA TAATCC-3' |
| PT109567r | SEQ ID No. 12 | 5'-TCACTGTCACTCTACAAAA CCG-3' |
| PT110048f | SEQ ID No. 13 | 5'-*TAAGGGGACTAGAGCAG GCTA-3' |
| PT110048r | SEQ ID No. 14 | 5'-TTCGATATTGAACCTTGG ACA-3' |
| Nuclear microsatellite primer pairs | | |
| 3011F | SEQ ID No. 15 | 5'-CACGACGTTGTAAAACGACA ATTTGGGTGTATTTTTCTT AGA-3' |
| 3011R | SEQ ID No. 16 | 5'-AAAAGTTGAAGGAGTTGGTG ATC-3' |
| 3034F | SEQ ID No. 17 | 5'-CACGACGTTGTAAAACGAC TCAAAATGCAAAAGACG-3' |
| 3034R | SEQ ID No. 18 | 5'-ATTAGGACTGGGGATGAT-3' |
| 6C12FF | SEQ ID No. 19 | 5'-CACGACGTTGTAAAACGAC CCAGACAACCCAAATGAAGG-3' |
| 6C12FR | SEQ ID No. 20 | 5'-GCCAGTGCAGACACAAA CAA-3' |

[1]asterisks denotes IRD 41 labeled nucleotide.
[2]The "F" and "R" in the primer pair names denote which primer in the primer pair is the forward and reverse primer.

DNA fragments containing nuclear microsatellite sequences were PCR-amplified from loblolly pine genomic DNA using 3 pairs of DNA primers. The DNA sequences for two primer pairs, PtTX3011 and PtTX3034, were obtained from the Texas A&M University web page of Dr. Claire Williams (http://forestry.tamu.edu/genetics/primer.txt). The other primer pair was designed from the loblolly pine EST sequence 6c12f (GenBank accession AA556811; see Table 2). This EST was found by conducting a BLAST search of EST sequences in GenBank using 10 repeats of the trinucleotide CAG. DNA sequence from the M13-29 forward sequencing primer was incorporated at the 5' end of each forward primer sequence (5'-CACGACGTTGTAAAAC-GAC-3' [SEQ ID No. 21], using the tailed primer strategy described by Oetting et al. (Genomics 30:450-458 (1995). An M13 primer with a 5' infrared fluorophore label, IRD41, was used as the only source of labeled primer for detection for all nuclear microsatellites. The PCR-reactions were carried out in 10 μl using 40 ng of loblolly pine genomic DNA as template. The PCR reactions contained PCR buffer and 1 unit of Taq polymerase (Boehringer Mannheim, 10 mM Tris-HCl, 1.5 mM MgCl2, 50 mM KCl, pH 8.3), 2 pmol anti-sense primer, 0.1 pmol IR-labeled sense primer, 0.1 mM dNTP (using dGTP). The reactions were run in 96-well polycarbonate microtitre plates (25 μL conical-bottom wells). The thermocycler temperature program was [94° C., 10 s; 65° C., 30 s; 72° C., 1 m] repeated 13 times, dropping the annealing temperature by 0.7 degree each cycle, followed by 23 cycles using the [94° C., 10 s; 56° C., 30 s; 72° C.]. The stop solution contained 95% formamide, 0.1 mM EDTA, 0.1% bromophenol blue, and 5 μL of stop solution was added to each reaction.

Electrophoresis: The DNA fragments were separated on an automated DNA sequencing apparatus (LI-COR 4000) using 0.25 mm gels (8% Long Ranger, FMC BioProducts) and 25 cm gel plates. The electrophoresis buffer was 1×TBE. The gels were run at 50° C. with constant power (70 W), and with the scanner collecting 16-bit video data with motor speed 3. The IRD-labeled STR molecular weight marker contained 15 DNA fragments that ranged from 50 to 350 bp (LI-COR). Loblolly pine accession 7-56 (NCSU-Industry Cooperative Tree Improvement Program, Raleigh) was used as a genotyping control sample for the cpDNA microsatellites. A 48-well comb was used, and each run contained 3 molecular weight marker standards, 6 control sample lanes, and 40 test sample lanes. For multiplexed runs, aliquots of 2 PCR reactions were loaded in each lane. The gel images were analyzed using RFLP-Scan software (Scanalytics, Billerica, Mass.). The software was used as an aid to facilitate scoring the size of the DNA fragments amplified from chloroplast DNA templates. The bands were analyzed for multiple peaks and "stutter" bands using quantitative peak profiles. Microsatellite fragments were classified by size using estimates of band migration rates relative to molecular weight markers and size standards.

Analysis

Exclusion probability for haplotypes was calculated using haplotype frequencies derived from the 78 first generation selections in group 1 and the 29 paternally unrelated individuals in the elite second group. For haplotype j, the exclusion probability was calculated as $$1-p_j, \qquad (3)$$

Where $p_j$ is the frequency of the jth haplotype.

The mean exclusion probability was calculated as $$\sum^{N_h} p_j^x (1-p_j) \qquad (4)$$

Where N is the total number of haplotypes.

EXAMPLE 4

Paternity Determination Using Microsatellite Polynucleotide Probes Derived from Nuclear and Chloroplast Genomes One aspect of the present invention provides a novel approach to breeding and testing that relies on determination of paternity or full pedigree of breeding cross progeny using DNA markers. The development of highly informative, PCR-derived, DNA markers and increasingly sophisticated analytical software has led to a marked improvement in the ability to assign parentage and determine relatedness in natural populations of many organisms (Marshall et al., *Mol. Ecol.* 7:639-655 (1998); O'Reilly et al., *Animal Gen.* 29:363-370 (1998); Goodnight and Queller, *Mol. Ecol.* 8:1231-1234 (1999); Hohoff and Brinkmann, *Mol. Biotech.* 13:123-136 (1999)). However, the DNA marker and analytical tools currently available have some shortcomings when dealing with the special circumstances resulting from the interbreeding of small, elite populations where many of the individuals are highly related to each other, as in the present invention. These shortcomings are discussed relative to DNA fingerprinting, paternity and pedigree analysis, along with choice of DNA marker and statistical analysis tools.

Choice of Molecular Marker

Microsatellites (SSRs, STRs)

Microsatellites (SSRs, STRs) have proven very useful for pedigree analyses (Blouin et al., *Mol. Ecol.* 3:393-401 (1996); Norris et al., *Aquaculture* 182:73-83 (2000)), and are generally considered the most powerful genetic marker available today (Goldstein and Pollock, *J. Hered.* 88:335-342 (1997)). Microsatellites are easily scored, reproducible, and highly variable, codominant markers. Most individuals in a population are heterozygous at SSR loci and few share the same genotype making them ideal for fingerprinting and determination of parentage (O'Malley and Whetten, In: *DNA markers: protocols, applications and overviews*, Caetano-Anolles and Gresshoff (eds.). John Wiley and Sons, New York (1997)). In the present study three highly variable nuclear microsatellites and seven chloroplast microsatellites were used (See Table 2 in Example 3). The latter are non-recombining, and like the Y-chromosome markers in humans (Hohoff and Brinkmann, *Mol. Biotech.* 13:123-136 (1999)) are paternally inherited in conifers (Neale et al., *Can. J. For. Res.* 16:1152-1154 (1986); Wagner, *New For.* 6:373-390 (1992)) making paternity assignment straightforward.

Chloroplast Simple Sequence Repeat Marker:

All of the 20 microsatellite primer pairs (Table 2, Example 3) designed by Vendramin et al. (*Mol. Ecol.* 5:111-114 (1996)) to amplify simple sequence repeat regions in the chloroplast genome of *Pinus thunbergii* were found to amplify similar size DNA fragments in *P. taeda* (data not shown). Data showing the distribution of the various polymorphic markers within a population of grandparents, parents, half-sibs and full-sibs pine trees is shown in Table 3. Seven of the 20 microsatellite primer pairs were found to generate DNA fragments that exhibited a simple pattern of inheritance that conformed with the expectation of uniparental inheritance from the pollen parent, and were considered sufficiently variable to be used in the present invention. Variation generally consisted of a series of single base pair differences. Unlike nuclear SSRs, the number of alleles per locus in these conifer cpSSRs was rather limited, varying from two to four.

Fifty different 7-locus haplotypes were detected in the natural and elite populations surveyed in this study. Fourteen additional haplotypes were detected in open-pollinated progeny from an ACP seed orchard (data not shown). Twenty of the 64 haplotypes were observed in the elite study population, several being shared by multiple selections, both related and unrelated (Table 3). Haplotype frequencies among the 29 paternally unrelated individuals in the elite group ranged from 0.034 to 0.103, and among unrelated individuals in the combined group, from 0.009 to 0.112. Combined, the five most common haplotypes in these two study groups occurred 42.4% of the time.

TABLE 3

Summary of molecular marker genotype data.

| Accession[1] | Half-sibs | Full-sibs | Known Parent | Known Grand Parent | Haplotype | Genotype[2] | | |
|---|---|---|---|---|---|---|---|---|
| | | | | | | 6C12F | 3011 | 3034 |
| 7 | | | | | 1 | 161/176 | 150/204 | 216/216 |
| 30 | 32m[3] | | 33m | | 4 | 173/176 | 135/238 | 220/212 |
| 17 | 19p, 21m | | | | 5 | 173/176 | 150/243 | 220/216 |
| 19 | 17p, 21m | | | | 5 | 161/176 | 189/243 | 218/216 |
| 3 | | | | | 5 | 170/173 | 150/150 | 230/228 |
| 8 | | | | | 7 | 182/191 | 231/255 | 228/216 |
| 15 | 16m | | | | 8 | 173/191 | 204/243 | 228/228 |
| 41 | | | | | 16 | 0 | 0 | 220/228 |
| 12 | | 13p | 14m | | 19 | 164/176 | 150/243 | 228/216 |
| 13 | | 12p | 14m | | 19 | 197/173 | 162/238 | 228/216 |
| 18 | | 20p, 22p | | | 19 | 173/176 | 150/150 | 224/214 |
| 20 | | 18p, 22p | | | 19 | 164/173 | 135/150* | 224/214 |
| 22 | | 18p, 20p | | | 19 | 173/176 | 150/162 | 228/224 |
| 24 | 26m | 25p | 27m | 45m | 19 | 167/182 | 201/243 | 216/216 |
| 25 | 26m | 24p | 27m | 45m | 19 | 167/182 | 201/204 | 226/216 |
| 1 | | | | | 28 | 167/173 | 150/232 | 224/220 |
| 32 | 30m | | 33m | | 29 | 164/176 | 168/238 | 226/212 |
| 35 | | | 43p | | 34 | 164/170 | 150/150 | 226/224 |
| 43 | | | | | 34 | 164/173 | 150/168 | 228/226 |
| 14 | | | | | 35 | 173/173 | 186/201 | 216/216 |
| 16 | 15m | | | | 35 | 173/173 | 135/150 | 226/220 |
| 37 | | | | | 35 | 173/173 | 150/168 | 226/216 |
| 38 | | | | | 36 | 161/176 | 150/204 | 228/224 |
| 4 | | | 5, 6m/p | | 37 | 164/164 | 150/150 | 224/216 |
| 5 | | | | | 37 | 164/164 | 150/150 | 224/222 |
| 6 | | | | | 37 | 164/173 | 150/150 | 216/216 |
| 2 | | | | | 37 | 161/173 | 204/261 | 226/220 |
| 10 | 9m | | 11p | | 42 | 164/173 | 150/201 | 226/216 |
| 11 | | | | | 42 | 167/173 | 135/201 | 226/226 |

TABLE 3-continued

Summary of molecular marker genotype data.

| | | | | | | Genotype[2] | | |
|---|---|---|---|---|---|---|---|---|
| Accession[1] | Half-sibs | Full-sibs | Known Parent | Known Grand Parent | Haplo-type | 6C12F | 3011 | 3034 |
| 34 | | | 42p | | 45 | 164/191 | 150/243 | 226/214 |
| 21 | 17m, 19m | | 23p | | 45 | 161/173 | 150/189 | 222/214 |
| 23 | | | | | 45 | 173/173 | 177/177 | 216/214 |
| 42 | | | | | 45 | 164/173 | 150/216 | 218/214 |
| 9 | 10m | | 11m | | 45 | 173/173 | 201/223 | 226/216 |
| 26 | 24m, 25m | | 27p | 45m | 48 | 167/176 | 150/204 | 228/226 |
| 27 | | | 45m | | 48 | 167/182 | 204/243 | 226/216 |
| 33 | | | | | 53 | 176/176 | 150/238 | 228/212 |
| 44 | | | | | 57 | 173/191 | 135/150 | 228/228 |
| 36 | 39p | 40p | 45p | | 60 | 182/191 | 162/243 | 226/220 |
| 39 | 36p, 40p | | 45p | | 60 | 173/182 | 135/243 | 226/226 |
| 40 | 39p | 36p | 45p | | 60 | 182/191 | 243/243 | 226/220 |
| 45 | | | | | 60 | 182/191 | 243/243 | 226/224 |
| 28 | 31p | 29p | 35m | 43p | 63 | 164/173 | 150/204 | 228/224 |
| 29 | 31p | 28p | 35m | 43p | 63 | 164/167 | 150/204 | 228/226 |
| 31 | 28p, 29p | | 34m | 42p | 63 | 164/164 | 150/150 | 216/214 |

[1]Accession number refers to known relatives within the breeding population.
[2]Genotypes include a 7-locus haplotype derived from chloroplast microsatellites and three diploid nuclear microsatellites.
[3]Accession number followed by parent origin i.e. m = maternal; p = paternal.

The mean exclusion probability for the multi-locus haplotypes in the elite group was 92.1% (the probability of excluding a non-sire), but this calculation assumes random mating among unrelated individuals. The 45 individuals in the elite group represent selections from 3 separate generations, many of which are related as grandparent-offspring, parent-offspring, half-sibs or full-sibs, both maternal and paternal (Table 3).

In the present pine breeding program databank, parentage gender is not maintained because reciprocal effects are virtually non-existent. As a consequence, chloroplast haplotypes were used to infer paternity/maternity for all levels of relationships (Table 3). In all cases but one, paternity could be verified with double exclusion (i.e., at least two cpSSR loci excluded one parent as being the father). In the exceptional case, accessions #5 and #6, parents of accession 4, shared the same haplotype and it was not possible to determine maternity or paternity for either using the relatively small number of loci assayed in this study. For the 45 individuals studied, there were 16 known cases of paternal haplotype identity by descent. Of the 20 haplotypes observed, ten occurred in only one selection, five were shared between two or more selections related by descent, four were shared between related and unrelated selections, and one was shared only among unrelated individuals (Table 3).

Nuclear Microsatellite Simple Sequence Repeat Markers:

One bi- (3034) and two tri (6c12f, 3011)-nucleotide repeat nuclear SSR loci were genotyped for all 45 elite selections (Table 3) and the population sample. The number of alleles per locus varied from 12 to 28 (select and population groups combined), with about 25% of the 54 total alleles occurring only once in the combined population. The frequency of the most common allele at each locus varied from 0.22 to 0.42. For two of the loci (3034 and 6c12f), gene frequencies in the elite test population and the population sample were similar. However, for locus 3011 they were dramatically different. Of the 28 alleles detected, only eight were shared by both populations. The natural population group had 12 private alleles, the elite population sample eight. The most common allele in the natural population (177; 0.52%) occurred in only one individual in the study population. The two populations used in the present study originated from geographically distinct areas in the eastern range of the species in the southeast United States. Williams et al. (*Heredity* 84:261-268 (2000)) have demonstrated populations of *P. taeda* from the eastern and western portions of the species range possess some private alleles, but the differences do not seem to be on the order noted here.

Twenty-one putative cases of either maternal—or paternal—offspring relatedness occurred in the elite population listed in Table 3. In three of these cases, nSSR genotypes were observed that were not consistent with expected genotypes. For example, accession 21 shared an appropriate haplotype with the putative father, accession 23, but did not share a common allele at nSSR 3011. Accessions 12 and 13, putative full-sibs, did not share a common allele with the putative mother (accession 14), at one locus in the case of accession 13, and at 2 loci in the case of accession 14 (Table 3). Such inconsistencies could have arisen by 1) inaccurate genotyping, 2) mutations, or 3) inaccurately labeled pedigree. The latter case is known to occur with higher than acceptable frequency in tree breeding (Adams et al., *Silv. Genet.* 37:147-152 (1988)). The routine use of markers in confirming parentage in progeny tests, as suggested here, would greatly reduce this occurrence.

DNA Fingerprinting Using Combined cpSSR and nSSR

The combination of paternally inherited cpSSR haplotypes and three Mendelian nSSR genotypes provided a unique fingerprint for each of the 45 selections in the present study, despite the appreciable level of relatedness between the parental trees. The addition of 2-3 more loci, either chloroplast or nuclear in origin, would likely add sufficient discriminating power to unambiguously fingerprint every individual in most pine breeding programs or clonal trials.

EXAMPLE 5

Pedigree Analysis

In the present study, the analytical software KINSHIP (Goodnight and Queller, *Mol. Ecol.* 8:1231-1234 (1999)) was used to estimate relatedness (probability of sharing an allele by descent) for all possible pairs of individuals (990 combinations) and for all potential hypothetical relationships. Based on known relationships, the program-estimated averages were reasonably accurate (Table 4), but variation about the mean was significant. Similar dispersion was noted in salmon (Norris et al., *Aquaculture* 182:73-83 (2000)). Furthermore, high estimates of relatedness were obtained for a number of unrelated pairs. Without the addition of many more loci, it is apparent that likelihood approaches to assigning parentage for both parents would not be precise enough to meet the needs of this scenario.

Table 4. Expected ($R_e$) and average (SE) observed estimates of relatedness (probability of sharing an allele by descent) for known pedigree relationships in the elite test population.

| Grandparent - Offspring N = 6 $R_e$ = 0.25 | Parent - Offspring N = 21 $R_e$ = 0.50 | Full-sibs N = 7 $R_e$ = 0.50 | Half-sibs N = 12 $R_e$ = 0.25 |
|---|---|---|---|
| 0.31 (0.10) | 0.44 (0.05) | 0.53 (0.09) | 0.31 (0.06) |

It should be noted that single locus or haplotype maternal exclusion can be developed relatively easily for conifers using maternally inherited mitochondrial DNA markers (Wagner, *New For.* 6:373-390 (1992)). Though variation is known to exist in mtDNA of conifers (Deverno et al., *Theor. and Appl. Genet.* 86:383-388 (1993); Dong and Wagner, *Theor. Appl. Genet.* 86:573-578 (1993); Aagard et al., *Mol. Ecol.* 4:441-447 (1995)) a suite of highly informative markers is not currently available for pine. Notable concerns for the development of mitochondrial genome markers would include high rates of mutation in hot spots and heteroplasmy (Wagner et al., *Theo. Appli. Genet.* 82:510-514 (1991); Hipkins et al., *For. Gen.* 1:179-189 (1994)).

While the preferred embodiment of the invention has been illustrated and described, it will be appreciated that various changes can be made therein without departing from the spirit and scope of the invention.

---

The embodiments of the invention in which an exclusive property or privilege is claimed are defined as follows:

1. A Loblolly pine tree breeding method comprising:
   (a) mixing pollen obtained from a breeding group comprising a plurality of parental Loblolly pine trees to obtain a pollen polymix;
   (b) pollinating female reproductive structures from each parental Loblolly pine tree in the plurality of Loblolly pine parental trees with the pollen polymix to obtain a plurality of progeny lots, wherein each progeny lot comprises seeds obtained from a different cross between the pollen polymix and each different Loblolly pine parental tree of the plurality of Loblolly pine parental trees;
   (c) evaluating progeny Loblolly pine trees grown from each of the progeny lots using objective criteria to obtain a phenotype score;
   (d) determining the pedigree of a plurality of Loblolly pine progeny trees using DNA analysis;
   (e) using the pedigree and phenotype score to identify a plurality of elite Loblolly pine trees having an acceptable level of relatedness for inclusion in a breeding group and
   (f) using the breeding group identified in step (e) in a next generation of tree breeding to produce an advanced generation of Loblolly pine trees having increased genetic gain.

2. The method of claim 1 additionally comprising selecting candidate Loblolly pine trees from within the progeny trees based upon their phenotype score, wherein step (d) is performed on the candidate Loblolly pine trees, and step (e) is performed using the pedigree and phenotype scores from the candidate Loblolly pine trees to identify elite Loblolly pine trees for use in the next generation of Loblolly pine tree breeding.

3. The method of claim 1, wherein the pedigree and phenotype scores are used to estimate the breeding values of a plurality of progeny and parental Loblolly pine trees, and the breeding values are used to identify the elite Loblolly pine trees for use in the next generation of Loblolly pine tree breeding.

4. The method of claim 3, wherein the elite Loblolly pine trees are derived from parental Loblolly pine trees that have a high general combining ability.

5. The method of claim 1, wherein the pedigree determined is paternity.

6. The method of claim 1, wherein the pedigree determined is paternity and maternity.

7. The method of claim 1, wherein the phenotype score is obtained for a phenotype selected from the group consisting of disease resistance, growth rate, growth habit, chemical composition of any plant tissue, drought resistance, temperature hardiness, elevation adaptation, fecundity, and any combination thereof.

8. The method of claim 1, wherein the DNA analysis is performed using a DNA analysis method selected from the group consisting of DNA sequencing, restriction fragment length polymorphism (RFLP), amplified fragment length polymorphism (AFLP), randomly amplified polymorphic DNA (RAPD), single nucleotide repeat microsatellites, di-, tri-, and tetra-nucleotide simple sequence repeats (SSRs), SSR-anchored PCR, sequenced tagged sites (STS), single nucleotide polymorphism (SNP), single stranded conformational polymorphism (SSCP), sequenced characterized amplified regions (SCAR), allele-specific associated primers (ASAP), single primer amplification reaction (SPARs), and cleaved amplified polymorphic sequences (CAP).

9. The method of claim 1, wherein a plurality of pollen polymixes are prepared, each pollen polymix comprised of pollen obtained from a plurality of different parental trees, each pollen polymix of the plurality of pollen polymixes being used to pollinate female reproductive structures from parental trees whose pollen or that of its close relatives are not represented in the pollinating pollen polymix.

10. The method of claim 1 wherein the DNA analysis method is performed using single nucleotide repeat microsatellite analysis.

11. A Loblolly pine tree breeding method comprising:
   (a) mixing pollen obtained from a breeding group comprising a plurality of parental Loblolly pine trees to obtain a pollen polymix;
   (b) pollinating female reproductive structures from each parental tree in the plurality of Loblolly pine parental trees with the pollen polymix to obtain a plurality of progeny lots, wherein each progeny lot comprises seeds obtained from a different cross between the pollen polymix and each different parental tree of the plurality of parental trees;

(c) evaluating progeny Loblolly pine trees grown from each of the progeny lots using objective criteria to obtain a phenotype score;

(d) determining the pedigree of a plurality of Loblolly pine progeny trees using DNA analysis; and (e) using the pedigree and phenotype score to identify a plurality of elite Loblolly pine trees having an acceptable level of relatedness for inclusion in a breeding group for use in a next generation of tree breeding to produce an advanced generation of Loblolly pine trees having increased genetic gain.

12. The method of claim 11, wherein the DNA analysis is performed using a DNA analysis method selected from the group consisting of DNA sequencing, restriction fragment length polymorphism (RFLP), amplified fragment length polymorphism (AFLP), randomly amplified polymorphic DNA (RAPD), single nucleotide repeat microsatellites, di-, tri-, and tetra-nucleotide simple sequence repeats (SSRs), SSR-anchored PCR, sequenced tagged sites (STS), single nucleotide polymorphism (SNP), single stranded conformational polymorphism (SSCP), sequenced characterized amplified regions (SCAR), allele-specific associated primers (ASAP), single primer amplification reaction (SPARs), and cleaved amplified polymorphic sequences (CAP).

13. The method of claim 11, wherein the DNA analysis method is performed using single nucleotide repeat microsatellite analysis.

* * * * *

SEQUENCE LISTING

```
<160> NUMBER OF SEQ ID NOS: 21

<210> SEQ ID NO 1
<211> LENGTH: 23
<212> TYPE: DNA
<213> ORGANISM: Artificial Sequence
<220> FEATURE:
<223> OTHER INFORMATION: Chloroplast Microsatellite Oligonucleotide
      Primer
<220> FEATURE:
<221> NAME/KEY: misc_feature
<222> LOCATION: (1)..(1)
<223> OTHER INFORMATION: Wherein C at position 1 is an IRD 41 labeled
      nucleotide

<400> SEQUENCE: 1
caattggaat gagaacagat agg                                             23

<210> SEQ ID NO 2
<211> LENGTH: 20
<212> TYPE: DNA
<213> ORGANISM: Artificial Sequence
<220> FEATURE:
<223> OTHER INFORMATION: Chloroplast Microsatellite Oligonucleotide
      Primer

<400> SEQUENCE: 2
tgcgttgcac ttcgttatag                                                 20

<210> SEQ ID NO 3
<211> LENGTH: 23
<212> TYPE: DNA
<213> ORGANISM: Artificial Sequence
<220> FEATURE:
<223> OTHER INFORMATION: Chloroplast Microsatellite Oligonucleotide
      Primer
<220> FEATURE:
<221> NAME/KEY: misc_feature
```

```
<222> LOCATION: (1)..(1)
<223> OTHER INFORMATION: Wherein A at position 1 is an IRD 41 labeled
      nucleotide

<400> SEQUENCE: 3
agaataaact gacgtagatg cca                                            23

<210> SEQ ID NO 4
<211> LENGTH: 24
<212> TYPE: DNA
<213> ORGANISM: Artificial Sequence
<220> FEATURE:
<223> OTHER INFORMATION: Chloroplast Microsatellite Oligonucleotide
      Primer

<400> SEQUENCE: 4
aattttcaat tcctttcttt ctcc                                           24

<210> SEQ ID NO 5
<211> LENGTH: 22
<212> TYPE: DNA
<213> ORGANISM: Artificial Sequence
<220> FEATURE:
<223> OTHER INFORMATION: Chloroplast Microsatellite Oligonucleotide
      Primer
<220> FEATURE:
<221> NAME/KEY: misc_feature
<222> LOCATION: (1)..(1)
<223> OTHER INFORMATION: Wherein C at position 1 is an IRD 41 labeled
      nucleotide

<400> SEQUENCE: 5
cccgtatcca gatatacttc ca                                             22

<210> SEQ ID NO 6
<211> LENGTH: 21
<212> TYPE: DNA
<213> ORGANISM: Artificial Sequence
<220> FEATURE:
<223> OTHER INFORMATION: Chloroplast Microsatellite Oligonucleotide
      Primer

<400> SEQUENCE: 6
tggtttgatt cattcgttca t                                              21

<210> SEQ ID NO 7
<211> LENGTH: 21
<212> TYPE: DNA
<213> ORGANISM: Artificial Sequence
<220> FEATURE:
<223> OTHER INFORMATION: Chloroplast Microsatellite Oligonucleotide
      Primer
<220> FEATURE:
<221> NAME/KEY: misc_feature
<222> LOCATION: (1)..(1)
<223> OTHER INFORMATION: Wherein T at position 1 is an IRD 41 labeled
      nucleotide

<400> SEQUENCE: 7
tcatagcgga agatcctctt t                                              21

<210> SEQ ID NO 8
<211> LENGTH: 21
<212> TYPE: DNA
<213> ORGANISM: Artificial Sequence
<220> FEATURE:
<223> OTHER INFORMATION: Chloroplast Microsatellite Oligonucleotide
      Primer
```

-continued

```
<210> SEQ ID NO 9
<211> LENGTH: 22
<212> TYPE: DNA
<213> ORGANISM: Artificial Sequence
<220> FEATURE:
<223> OTHER INFORMATION: Chloroplast Microsatellite Oligonucleotide
      Primer
<220> FEATURE:
<221> NAME/KEY: misc_feature
<222> LOCATION: (1)..(1)
<223> OTHER INFORMATION: Wherein T at position 1 is an IRD 41 labeled
      nucleotide

<400> SEQUENCE: 9
ttcattggaa atacactagc cc                                              22

<210> SEQ ID NO 10
<211> LENGTH: 21
<212> TYPE: DNA
<213> ORGANISM: Artificial Sequence
<220> FEATURE:
<223> OTHER INFORMATION: Chloroplast Microsatellite Oligonucleotide
      Primer

<400> SEQUENCE: 10
aaaaccgtac atgagattcc c                                               21

<210> SEQ ID NO 11
<211> LENGTH: 25
<212> TYPE: DNA
<213> ORGANISM: Artificial Sequence
<220> FEATURE:
<223> OTHER INFORMATION: Chloroplast Microsatellite Oligonucleotide
      Primer
<220> FEATURE:
<221> NAME/KEY: misc_feature
<222> LOCATION: (1)..(1)
<223> OTHER INFORMATION: Wherein T at position 1 is an IRD 41 labeled
      nucleotide

<400> SEQUENCE: 11
tattatcgaa caacgagaat aatcc                                           25

<210> SEQ ID NO 12
<211> LENGTH: 22
<212> TYPE: DNA
<213> ORGANISM: Artificial Sequence
<220> FEATURE:
<223> OTHER INFORMATION: Chloroplast Microsatellite Oligonucleotide
      Primer

<400> SEQUENCE: 12
tcactgtcac tctacaaaac cg                                              22

<210> SEQ ID NO 13
<211> LENGTH: 21
<212> TYPE: DNA
<213> ORGANISM: Artificial Sequence
<220> FEATURE:
<223> OTHER INFORMATION: Chloroplast Microsatellite Oligonucleotide
      Primer
<220> FEATURE:
<221> NAME/KEY: misc_feature
<222> LOCATION: (1)..(1)
<223> OTHER INFORMATION: Wherein T at position 1 is an IRD 41 labeled
      nucleotide
```

<400> SEQUENCE: 8
cggattgatc ctaaccatac c                                               21

```
<400> SEQUENCE: 13 taagggact agagcaggct a                                          21

<210> SEQ ID NO 14
<211> LENGTH: 21
<212> TYPE: DNA
<213> ORGANISM: Artificial Sequence
<220> FEATURE:
<223> OTHER INFORMATION: Chloroplast Microsatellite Oligonucleotide
      Primer

<400> SEQUENCE: 14
ttcgatattg aaccttggac a                                         21

<210> SEQ ID NO 15
<211> LENGTH: 42
<212> TYPE: DNA
<213> ORGANISM: Artificial Sequence
<220> FEATURE:
<223> OTHER INFORMATION: Nuclear Microsatellite Oligonucleotide Primer

<400> SEQUENCE: 15
cacgacgttg taaaacgaca atttgggtgt attttctta ga                  42

<210> SEQ ID NO 16
<211> LENGTH: 23
<212> TYPE: DNA
<213> ORGANISM: Artificial Sequence
<220> FEATURE:
<223> OTHER INFORMATION: Nuclear Microsatellite Oligonucleotide Primer

<400> SEQUENCE: 16
aaaagttgaa ggagttggtg atc                                       23

<210> SEQ ID NO 17
<211> LENGTH: 36
<212> TYPE: DNA
<213> ORGANISM: Artificial Sequence
<220> FEATURE:
<223> OTHER INFORMATION: Nuclear Microsatellite Oligonucleotide Primer

<400> SEQUENCE: 17
cacgacgttg taaaacgact caaaatgcaa aagacg                         36

<210> SEQ ID NO 18
<211> LENGTH: 18
<212> TYPE: DNA
<213> ORGANISM: Artificial Sequence
<220> FEATURE:
<223> OTHER INFORMATION: Nuclear Microsatellite Oligonucleotide Primer

<400> SEQUENCE: 18
attaggactg gggatgat                                             18

<210> SEQ ID NO 19
<211> LENGTH: 39
<212> TYPE: DNA
<213> ORGANISM: Artificial Sequence
<220> FEATURE:
<223> OTHER INFORMATION: Nuclear Microsatellite Oligonucleotide Primer

<400> SEQUENCE: 19
cacgacgttg taaaacgacc cagacaaccc aaatgaagg                      39
```

```
-continued

<210> SEQ ID NO 20
<211> LENGTH: 20
<212> TYPE: DNA
<213> ORGANISM: Artificial Sequence
<220> FEATURE:
<223> OTHER INFORMATION: Nuclear Microsatellite Oligonucleotide Primer

<400> SEQUENCE: 20
gccagtgcag acacaaacaa                                              20

<210> SEQ ID NO 21
<211> LENGTH: 19
<212> TYPE: DNA
<213> ORGANISM: Artificial Sequence
<220> FEATURE:
<223> OTHER INFORMATION: Chloroplast Microsatellite Oligonucleotide
      Primer

<400> SEQUENCE: 21
cacgacgttg taaaacgac                                               19
```